United States Patent [19]

Cohen et al.

[11] Patent Number: 4,732,852

[45] Date of Patent: Mar. 22, 1988

[54] SITE DIRECTED PEPTIDASE CLEAVAGE

[75] Inventors: Stanley N. Cohen, Portola Valley; Annie C. Y. Chang, Palo Alto, both of Calif.

[73] Assignee: Cetus Corporation, Emeryville, Calif.

[21] Appl. No.: 642,755

[22] Filed: Aug. 20, 1984

Related U.S. Application Data

[63] Continuation of Ser. No. 323,347, Nov. 20, 1981, abandoned.

[51] Int. Cl.4 .............................................. C12P 21/00
[52] U.S. Cl. ........................................ 435/68; 435/69; 435/172.3; 435/272; 435/810; 530/412; 530/413

[58] Field of Search ................ 435/68, 69, 172.1, 272, 435/810, 172.3; 530/412, 413, 810

[56] References Cited

U.S. PATENT DOCUMENTS 4,231,999 11/1980 Carlsson et al. .................... 435/7
4,350,764 9/1982 Baxter et al. ....................... 435/69

Primary Examiner—Robert J. Warden
Assistant Examiner—Stephen C. Wieder
Attorney, Agent, or Firm—Bertram Rowland; Gladys H. Monroy; Albert P. Halluin

[57] ABSTRACT

Method for preparing peptides free of undesired amino acids or amino acid sequences employing site specific receptors and proteases to cleave unprotected enzymatically hydrolyzable bonds.

16 Claims, 1 Drawing Figure

SITE DIRECTED PEPTIDASE CLEAVAGE

This is a continuation of application Ser. No. 323,347 filed Nov. 20, 1981, now abandoned.

BACKGROUND OF THE INVENTION

Field of the Invention

In many instances, polypeptides are available which have one or more undesired amino acids or amino acid sequences. This situation has become of acute importance with the use of hybrid DNA technology to produce a wide variety of polypeptides of physilogical interest. In many situations, amino acid sequences are obtained which may include one or more peptides of physilogical interest or peptides having an undesired presequence or undesired initial amino acids. This can be a result of other requirements which require that the preparation of the polypeptide include the presence of the undesired amino acids or that convenience makes it desirable to produce a group of peptides on the same chain. In some situations, flanking DNA sequences may be expressed.

In these situations, it would be desirable to be above to remove the sequences or excise the desired peptide from the extended polypeptide. Therefore, ways have to be devised where polypeptides may be modified by removal of terminal amino acids or terminal sequences or by cleavage at predetermined sites to excise a peptide of the desired composition.

SUMMARY OF THE INVENTION

A method is provided for selectively cleaving a peptide bond to obtain peptide product free of an undesired amino acid or amino acid sequence. Receptor, usually antibodies, to specific determinant sites are combined with the initial peptide to protect labile bonds present in the peptide product, while allowing cleavage of unprotected bonds. The receptor bound initial peptide is combined with a peptidase under hydrolysing conditions resulting in cleavage of the unprotected peptide bond. The peptide product is then freed of the receptor and isolated.

BRIEF DESCRIPTION OF THE DRAWINGS

The FIGURE is a photograph of an electrophoresis gel showing the results outlined in the Experimental section herein.

DESCRIPTION OF THE SPECIFIC EMBODIMENTS

Figure 1:
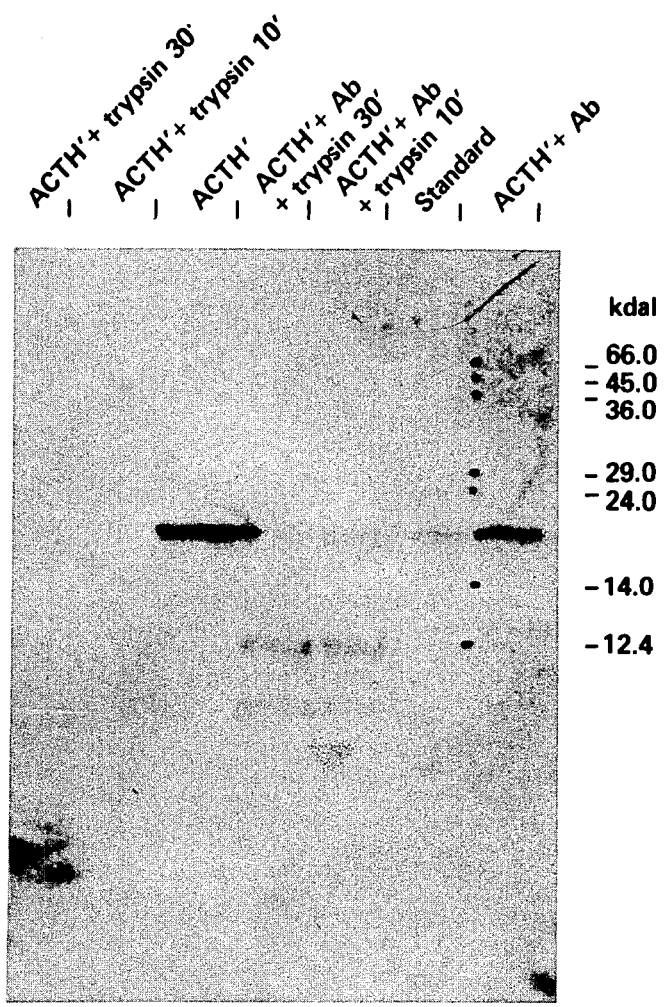

The subject method provides a simple and conventient means for removing an amino acid or amino acid sequence from a polypeptide to provide a product free of the undesired amino acid or amino acid sequence. The method finds particular use in a number of situations where fused or extended peptides are available, either as naturally occurring, or synthesized, particularly by means of hybrid DNA technology.

Many naturally occurring peptides and proteins exist naturally having two or more peptide sequences which are excised in vivo from the initial peptide or protein to provide a product having physiological activity. Where these naturally occurring peptides or proteins can be isolated, it may be desirable to cleave the peptide or protein so as to obtain the compound having physiological activity. In other situations, prodrugs may be involved, where it may be desirable to remove the presequence, so as to isolate the drug. Other situations may involve removing sequences to restrict the product to one or more determinant sites which bind to a receptor to determine the receptor binding site, or the like.

With hybrid DNA technology many of the same or similar considerations will also be involved. In addition, there will be those situations peculiar to hybrid DNA technology. With small peptides, it may be difficult to isolate the peptide due to substantial degradation of the peptide while retained in the microorganism host cell. Therefore, it may be necessary to include with the peptide of interest a presequence which protects the desired product from substantial degradation. In other situations, it may be convenient or necessary to have a fused product which includes two or more peptides of interest. After isolation of the desired product it will be necessary to cleave the product to provide the peptides having physiological activity.

Where the fused product is obtained from messenger RNA which codes for the fused product naturally, there will normally be a labile bond between the two peptides of interest. Therefore, by protecting one or both of the peptides, one can cleave the labile bond between the two peptides and isolate the two peptides separate from one another. Alternatively, one may allow one or the other of the two peptides to be degraded, so as to leave the peptide of interest.

In some instances, there may be an extra terminal amino acid or terminal amino acid sequence due to the specific characteristics of hybrid DNA technology. For example, with many mammalian peptides and proteins, the peptides and proteins lack an N-terminal methionine. However, the peptides are initially prepared in vivo with an initiating formyl-methionine, which in the mammalian cell is removed to provide N-terminal methionine free peptide or protein. Since the manner in which this is removed in the mammalian cell may not be present in a microorganism host, the resulting product would have an unnatural N-terminal methionine on the mammalian peptide or protein of interest. Again, it would be desirable to be able to remove the N-terminal methionine without removing additional amino acids.

Based on the amino acid sequence of the peptide, one can frequently predict the nature of folding of the peptide and the probable amino acid sequence of amino acids at the determinant site. Therefore, based on the knowledge of the amino acid sequence, one can prepare small polypeptides, normally at least nonapeptides and use these as haptens to prepare antibody to the specific determinant sites which are to be protected. In this manner, areas of the peptide or protein of interest can be readily protected while leaving exposed areas to be removed or hydrolyzed. Thus, great versatility can be achieved with peptides and proteins prepared by hybrid DNA technology, since once the peptide is prepared, one can protect the peptide insert of interest while allowing other portions to be hydrolyzed.

Where the peptide to be acted upon includes one or more peptide sequences of interest, which are also naturally available, one can use a naturally available compound as a hapten or immunogen to prepare antibodies which will then act to protect the peptide sequence of interest. Additionally, for naturally occurring compounds, in many instances there are natural receptors which can be isolated and employed instead of having to prepare antibodies.

The antibodies may be monoclonal or polyclonal. Where the peptide of interest is relatively large with a plurality of determinant sites, polyclonal antibodies may be advantageous, while where the peptide sequence of interest has only a few determinant sites, monoclonal antibodies may prove to be of greater utility. With polyclonal antibodies, if the sequence to be cleaved is a determinant site, a mimetic oligopeptide may be prepared to block and/or remove antibody binding to this site in antiserum employing affinity chromatography or other specific technique.

The antibodies which are used may be whole antibodies or fragments thereof, such as Fab fragments or F(ab)'$_2$ or other fragment which has binding specificity. The particular immunoglobulin which is employed is not critical, although normally IgG will be used.

Normally, the sequences of interest will be at least 10 amino acids, more usually at least 12 amino acids, and frequently 16 or more amino acids. Generally, the amino acid sequence will be not greater than about 500 amino acids, more usually not greater than about 250 amino acids, and may be not more than about 200 amino acids. The initial polypeptide which is treated will generally not exceed about 1000 amino acids, more usually not exceeding about 500 amino acids, and frequently not exceeding about 200 amino acids. The initial peptide will usually be at least 12 amino acids, more usually at least about 16 amino acids and generally 24 amino acids or more.

As illustrative of a wide variety of peptides and proteins which can be either isolated from natural sources or produced by hybrid DNA technology are the following:
interferons, e.g. lumphoblastoid, leukocyte, fibroblastoid and immune, thymosin, somatostatin, luteinizing hormone, chorionicgonadototropin, $\beta$-lipotropin, $\beta$-endorphin, dynorphin, colony stimulating factor, angiotensinogen, bradykinin, IgA, IgD, IgE, IgG and IgM, histocompatibility antigens, capsid proteins, carcinoembryonic antigen, pepsinogen, trypsinogen, chymotrypsinogen, plasminogen, fibrinogen, melanocyte stimulating hormone, hemoglobin, myoglobin, serum albumin, thyroglobulin, actin, myosin, cascin, hemocyanin, thyrotropic hormone, histone, DNase, RNase, follicle stimulating hormone, insulin, glucagon, oxytocin, their mimetic analogs, etc.

It is to be understood that these peptides and proteins would be joined to another sequence because of: the nature of their naturally occurring form: being derived from a source other than the source intended for the compound: or being prepared by hybrid DNA technology. Regardless of the manner in which the extended peptide or protein is obtained, the treatment will normally be the same.

After obtaining the initial extended peptide (including protein) which is to be hydrolytically cleaved by a peptidase, the peptide is combined with the receptor, normally an antibody, under binding conditions. Normally, the conditions will be aqueous buffered solutions and mild temperatures generally from about 0° to 30° C. and pH's ranging from about 7 to 9. A sufficient amount of the receptor will be added to substantially saturate the complementary binding sites. Therefore, at least a stoichiometric amount based on binding sites will be used, normally an excess, which may be 2-fold or higher. The concentration of the peptide may be varied widely, generally ranging from about 1$\mu$M to 1M. The concentration is one of convenience, and not critical to this invention. The time for the reaction between the peptide and its receptor will be sufficient to provide complete binding, usually requiring at least 30 min., and generally requiring not more than about 24 hr.

After completion of binding, a peptidase is added and the composition of the solution and temperature may or may not be changed, depending upon the peptidase. Particularly, where a low temperature has been employed to enhance the binding affinity of the receptor, the temperature may now be raised to enhance the rate of hydrolytic cleavage. The amount of enzyme which will be added is not critical to this invention, but a sufficient amount should be added to insure a rapid rate of reaction. Generally, the molar concentration of enzyme will be less than the molar concentration of peptide, frequently, two to three orders of magnitude less. The amount of enzyme employed will vary with the turnover rate of the enzyme, availability, concentration of the initial peptide to be cleaved, presence of proteinaceous compounds other than the peptides of interest, and the like. Various peptidases can be used, depending upon the nature of the bond to be cleaved. That is, wheter the amino acid to be removed is a terminal amino acid or an internal peptide bond is to be cleaved. In addition, the nature of the amino acid on one or opposite sides of the bond to be cleaved and whether there is to be random cleavage or specific cleavage will determine the peptidase. Various peptidases include trypsin, pepsin, chymotrypsin, carboxypeptidase A, bromelain, papain, leucine aminopeptidase, dipeptidases, prolidase, pronase, thermolysin, rennin, cathepsin. Where a peptidase is available which is specific for a unique peptide bond to be cleaved, this invention is not applicable since protection is not required. Therefore, there will be at least two hydrolytically susceptible bonds in the peptide to be cleaved.

After sufficient time for the peptidase reaction, the enzyme reaction will be terminated, which can be achieved by employing an inhibitor, particularly a noncompetitive inhibitor, by rapid separation of the proteins, e.g. centrifugation or employing enzyme bound to a support, where the enzyme and the peptide of interest bound to a receptor are of substantially different molecular weights, or a change in the reaction conditions, which substantially diminishes the turnover rate of the enzyme e.g. reduction in temperature, followed by separation.

The manner in which the enzyme reaction is terminated is not critical and will vary depending upon the nature of the materials, the size of the reaction mixture, as well as economic considerations.

The peptide or protein of interest may then be isolated by any means which allows for separation of the peptide of interest from its receptor and isolation of the peptide without destruction of its desired properties. This can involve heat, generally temperatures in excess of about 60° C., high salt concentrations, generally in excess of about 2M, high urea concentrations, usually greater than about 2M, or the like. After destruction of the ligand-receptor complex, the peptide or protein of interest may be separated from the receptor by any convenient means, such as electrophoresis, chromatography, isopycnic centrifugation, gradient density centrifugation, and the like.

In one mode, the receptors may be bound to a support. Conveniently, the receptors bound to the support may then be loaded onto a column and the same to be treated passed through the column so as to become bound to the receptors. All of the non-specifically bound material may then be removed by washing, followed by introduction of the enzyme solution which will cleave the undesired portion of the initial peptide or protein. The cleaved peptides will be washed through the column, followed by treating the column, conveniently with a high ionic strength solution, to release the peptide of interest free of other material. In this way the column could be repetitively used until it lost its affinity for the ligand.

The materials for the column can be supplied as a kit. The receptor(s), usually antibodies, may be bound to a wide variety of particles, either covalently or non-covalently. Polystyrene, polyacrylamides, glass, silicons of the like can serve as porour or non-porous particles, generally ranging in size from about $10\mu$ to 2 mm. Included with the particles would be the peptidase, normally as a lyophilized powder, with other additives, such as buffer, preservatives, inert protein or the like. For convenience, reagents can be provided for breaking the receptor peptide complex.

In order to demonstrate the subject invention, the following examples are offered by way of illustration and not by way of limitation.

EXPERIMENTAL

The plasmid pKOM-2 was prepared as follows. A 2.7 kb EcoRI fragment from a fetal liver DNA genomic library containing the coding sequence for human ACTH-$\beta$-LPH spanning from amino acid $-92$ of the amino terminus of pro-opio-melanocortin to the carboxyl terminus of $\beta$-LPH was cloned into the EcoRI site of pBR322 (Chang et al., PNAS USA (1980) 77:4890–4894). From the plasmid thus obtained, a 450bp AvaI/SalI fragment was excised which stretches 51bp upstream from the first base of ACTH to 30bp after the stop codon of $\beta$-LPH and inserted into pACYC184 to yield pACYC621. A 1200bp fragment carrying the E. coli recA regulatory signals including the promoter, ribosomal binding site, and initiation codon, obtained by g/ I restriction of pOG2180 followed by $S_1$ nuclease treatment, was inserted into pACYC621 at an AvaI restriction site which has been blunt ended with $S_1$ nuclease. The ACTH-$\beta$-LPH genes are in reading frame with the initiation codon of the recA regulatory signals. The resulting plasmids were cloned in E. coli PM191(recA$^-$) and the plasmid from one of the clones was excised with BamHI/SalI to provide a fragment having both the recA regulatory signals and the ACTH-$\beta$-LPH genes which was inserted into the m/HI/I/ I site of pBR322 to provide pKOM-2.

The plasmid clone pKOM-2 carrying the genes encoding human ACTH-$\beta$-LPH was transformed into a minicell carrying strain E. coli DS410. In the minicells, the peptides were synthesized from the genes present in the plasmid DNA and not from the host chromosomes. Minicells were isolated on a sucrose gradient, resuspected in Mg medium supplemented with amino acids, preincubated at 30° C. for 20 min, $^{35}$S methionine was then added and the minicells further incubated at 30° C. for 30 min.

The minicells were lysed in the loading buffer (0.07M Tris, pH6.8, 12% glycerol, 0.01% bromophenol blue and 3% sodium dodecyl sulfate), boiled at 95–100° C. for 5 min. and run on a 12.5% polyacrylamide gel. The gel was autoradiographed at 4° C. for 30 hrs., the band corresponding to the fused ACTH-$\beta$-LPH peptide was cut from the gel, washed in 25% isopropanol and then washed in 10% methanol to remove sodium dodecyl sulfate. The gel pieces were then dried by lyophilization and resuspended in 1 ml 0.1M NH$_4$HCO$_3$ pH 8.0 and incubated at 37° C. for 30 hrs.

The eluted peptide was lyophilized and resuspended in 100$\lambda$ 50 mM Tris pH8.0, three 10 $\mu$l samples were taken and incubated with an equal volume of antiserum to ACTH (1–24) at 4° C. for 18 hrs. while three 10 $\mu$l aliquots of a buffered solution containing 50 $\mu$g/ml bovine serum albumin were added to the rest of the samples and incubated under the same conditions. One $\mu$g amount of trypsin was then added to all samples, incubated at 37° C. for 0 min., 10 min. and 30 min. respectively, the reaction was stopped by the addition of 2 mM phenylmethylsulfonyl fluoride (PMSF), 20 $\mu$l of 2$\times$ loading buffer, boiled for 5 min and electrophoresed on a 10–30% polyacrylamide gel and autoradiographed. From the picture, two specific bands were present on the gel, when the ACTH fused peptide was reacted with the antiserum to ACTH (1–24) and treated with trypsin, no bonds were seen in the control samples.

As evidenced by the above results, the subject invention provides a novel and efficient way to remove undesired amino acids or amino acid sequences fused to a peptide or protein of interest. Thus, the subject invention can be used particularly advantageously with peptides produced by hybrid DNA technology, where for a variety of reasons the peptide of interest cannot be directly produced, but must be made in combination with an additional amino acid or amino acid sequence or fused to one or more other peptides. Thus, the subject method when used in conjunction with hybrid DNA technology greatly enhances the flexibility of the hybrid DNA technology in allowing for the production of peptide products which include sequences other than the sequence of interest, which sequences can be subsequently removed in accordance with the subject invention.

Although the foregoing invention has been described in some detail by way of illustration and example for purposes of clarity of understanding, it will be obvious that certain changes and modifications may be practiced within the scope of the appended claims.

What is claimed is:

1. A method for specifically reducing the size of an extended peptide to a desired peptide product comprising:

combining an extended peptide with at least one antibody specific for an antigenic determinant site of said extended peptide to protect an enzymatically hydrolyzable labile bond from peptidase cleavage to produce an antibody bound peptide, wherein said antibody is selected to protect a selected region of said polypeptide;

combining said antibody bound peptide with a peptidase under conditions to provide hydrolytic cleavage of at least one exposed labile bond; and isolating said peptide product of said hydrolytic cleavage free of antibody.

2. A method according to claim 1, wherein said peptidase is trypsin.

3. A method according to claim 1, wherein said hydrolytically labile bond is a bond between two basic amino acids.

4. A method according to claim 3, wherein said basic amino acids are arginine or lysine.

5. A method according to claim 1, wherein said initial peptide is of from about 12 to 200 amino acids.

6. A method for preparing a peptide employing hybrid DNA technology involving a DNA sequence coding for said peptide and at least one flanking amino acid resulting in an extended peptide, said method comprising:

growing host cells containing a DNA sequence under conditions where said DNA sequence is expressed to produce an extended peptide;

isolating said extended peptide and combining said extened peptide substantially free of said host cells with an antibody of at least one idiotype specific for an antigenic determinant site of said extended peptide to protect an enzymatically hudrolyxable labile bond from peptidase cleavage to produce an antibody bound extened peptide, wherein said antibody is selected to protect a selected region of said polypeptide;

combining said antibody bound extened peptide with a peptidase under conditions to provide hydrolytic cleavage of at least one exposed labile bond; and isolating a peptide product of said hydrolytic cleavage free of antibody.

7. A method according to claim 6, wherein said host cell is a microorganism.

8. A method according to claim 7, which includes the additional step of lysing said host cells prior to isolating said extended polypeptide.

9. A method according to any of claim 6, wherein said peptidase is trypsin.

10. A method for specifically reducing the size of an extended peptide to a desired peptide product comprising:

combining an extended peptide with an antibody of at least one idiotype specific for an antigenic determinant site to protect an enzymatically labile bond from peptidase cleavage to produce an antibody bound peptide, wherein said antibody is bound to a support;

combining said antibody bound extened peptide with a peptidase under conditions to provide hydrolytic cleavage of at least one exposed labile bond;

treating the resulting antibody bound peptide product with a reagent solution to free said peptide product from said antibody; and separating said peptide product from said antibody.

11. A method according to claim 10, wherein said support is particles formed as a column; said extended peptide is combined with said antibodies by passing a solution of said extended peptide through said column, and thereafter passing a solution of said peptidase through said column, followed by passing said reagent solution through said column for releasing peptide product from said antibodies.

12. A kit for specifically reducing the size of an extended peptide to a desired peptide product comprising in packaged combination a multi-container unit having:

a first container containing antibodies specific for an antigenic determinant of an extended protein wherein the antibodies protect an enzymatically hydrolyzable labile bond while leaving at least one enzymatically hudrolyzable bond exposed to peptidase hydrolysis, said antibodies being bound to a support;

a second container containing a peptidase capable of cleaving said labile bond.

13. A kit according to claim 12 wherein the multi-container unit has a third container containing reagent for destroying antibody-peptide complex 14. A kit according to claim 13, wherein said peptidase is lyophilized.

15. A method according to claim 7, wherein said pepidase is trypsin.

16. A method according to claim 8, wherein said pepidase is trypsin.

* * * * *